US00PP22045P2

(12) United States Plant Patent
Giesen

(10) Patent No.: US PP22,045 P2
(45) Date of Patent: Jul. 26, 2011

(54) ***SOLENOSTEMON* PLANT NAMED 'MOS ROSBAST'**

(50) Latin Name: *Solenostemon scutellarioides*
Varietal Denomination: Mos Rosbast

(75) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/807,518

(22) Filed: Sep. 8, 2010

(51) Int. Cl.
*A01H 5/00* (2006.01)

(52) U.S. Cl. ..... Plt./373

(58) Field of Classification Search ..... Plt./373
See application file for complete search history.

*Primary Examiner* — Kent L Bell
(74) *Attorney, Agent, or Firm* — S. Matthew Edwards

(57) ABSTRACT

A new *Solenostemon* plant named 'Mos Rosbast' particularly distinguished by the bold slightly mottled red hues in the center of the foliage, with greyed-purple borders and yellow-green margins, with an upright, well branched and uniform plant habit.

1 Drawing Sheet

Latin name of the genus and species of the plant claimed: *Solenostemon scutellarioides.*

Varietal denomination: 'Mos Rosbast'.

BACKGROUND OF THE NEW PLANT

The present invention comprises a new *Solenostemon*, botanically known as *Solenostemon scutellarioides*, and hereinafter referred to by the variety name 'Mos Rosbast'.

'Mos Rosbast' is a product of a planned breeding program. The new cultivar has bold slightly mottled red hues in the center of the foliage with greyed-purple borders and yellow-green margins, with an upright, well branched and uniform plant habit.

'Mos Rosbast' originated from a hybridization made in January 2006 in a controlled breeding environment in Andijk, Netherlands. The female parent was the unpatented proprietary plant designated 'CS06-29-1' with less intense foliage color, larger foliage size and thinner stems.

The male parent of 'Mos Rosbast' was an unpatented proprietary plant identified as 'CS06-1-1' with less rose color in the foliage, smaller foliage size, and has less of a crenate margin. The resultant seed was sown in July 2006.

'Mos Rosbast' was selected as one flowering plant within the progeny of the stated cross in September 2006 in a controlled environment in Andijk, Netherlands.

The first act of asexual reproduction of 'Mos Rosbast' was accomplished when vegetative cuttings were propagated from the initial selection in September 2006 in a controlled environment in Andijk, Netherlands.

BRIEF SUMMARY OF INVENTION

Horticultural examination of plants grown from cuttings of the plant initiated in September 2006, and continuing thereafter, has demonstrated that the combination of characteristics as herein disclosed for 'Mos Rosbast' are firmly fixed and are retained through successive generations of asexual reproduction.

'Mos Rosbast' has not been observed under all possible environmental conditions. The phenotype may vary significantly with variations in environment such as temperature, light intensity and day length.

A Plant Breeder's Right for this cultivar was applied for in Canada on Feb. 18, 2010 (#10-6844). 'Mos Rosbast' has not been made publicly available more than one year prior to the filing of this application.

The following traits have been repeatedly observed and are determined to be basic characteristics of the new variety. The combination of these characteristics distinguishes this *Solenostemon* as a new and distinct variety.

BRIEF DESCRIPTION OF THE PHOTOGRAPHS

The accompanying photographic drawing shows typical foliage characteristics of 'Mos Rosbast' with colors being as true as possible with an illustration of this type. The photographic drawing shows a potted plant of the new variety.

DETAILED BOTANICAL DESCRIPTION

The plant descriptions, measurements and aforementioned photographs were taken in mid-June 2010 in Andijk, Netherlands. These plants were about 12 weeks old grown in a greenhouse in a bench trial in 4 inch pots.

Color references are made to The Royal Horticultural Society Colour Chart (R.H.S.) 2001.

TABLE 1

DIFFERENCES BETWEEN THE NEW VARIETY 'MOS ROSBAST' AND A SIMILAR VARIETY

| | 'Mos Rosbast' | 'Copper' (U.S. Plant Pat. No. 14,394) |
|---|---|---|
| Plant height: | About 32-40 cm | About 26 cm |
| Branch length: | 24-32 cm | About 24 cm |
| Foliage shape: | Ovate | Deltoid |

Plant:

*Form, growth and habit.*—Annual potted or garden plant grown for its distinctive and colorful foliage; Stems strong, upright and freely branching depending on the type and timing of terminal pinching; moderately vigorous growth habit.

*Plant height.*—About 32-40 cm.

*Plant width.*—32-38 cm.

*Garden performance and tolerance to weather.*—Very good.

Roots:

*Number of days to initiate roots.*—About 4 days at about 22 degrees C.

*Number of days to produce a rooted cutting.*—6-8 days at 22 degrees C.

*Type.*—Fine, fibrous, free branching.

*Color.*—RHS N155B but whiter.

Foliage:

*Arrangement.*—Opposite, simple.

*Immature, leaf color, upper surface.*—The center color closest to RHS 51B in varying proportions of the leaf; with closest to RHS 183A darker borders and RHS 144B margins.

*Lower surface.*—RHS 51A in the center of the leaf, with a border of about RHS 183C and RHS 145B margins.

*Mature, leaf color, upper surface.*—The center color of between RHS 50A and RHS 50B in varying proportions of the leaf, with small blotches of the same colors mixed in; a darker border of closest to RHS 183A in varying proportions of the leaf; and with margins of RHS 145A.

*Lower surface.*—RHS 51A in the center of the leaf, with a border of about RHS 183C and RHS 145B margins.

*Length.*—8.5-10.5 cm.

*Width.*—4.1-6.3 cm.

*Shape.*—Ovate.

*Base shape.*—Attenuate.

*Apex shape.*—Acuminate.

*Margin.*—Crenate to slightly serrulate.

*Texture, upper surface.*—Pubescent, hirsute.

*Lower surface.*—Pubescent, hirsute mainly on the veins.

*Color of veins, upper surface.*—About RHS 59B.

*Color of veins, lower surface.*—About RHS 60B.

*Petiole color.*—RHS 144D.

*Length.*—2.2-2.4 cm.

*Diameter.*—0.3-0.5 cm.

*Texture.*—Pubescent, scattered pilose.

Stem:

*Quantity of main stem per plant.*—5-8.

*Color of stem.*—RHS 60D.

*Length of stem.*—24-32 cm.

*Diameter.*—0.7 cm.

*Length of internodes.*—2.8-6.8 cm.

*Texture.*—Pubescent, pilose at axis.

Inflorescence: Flowering development was not observed on this plant to this date. Therefore also, seed development has not been observed.

Disease/pest resistance: Disease/pest resistance has not been observed.

What is claimed is:

1. A new and distinct variety of *Solenostemon* plant named 'Mos Rosbast' substantially as illustrated and described herein.

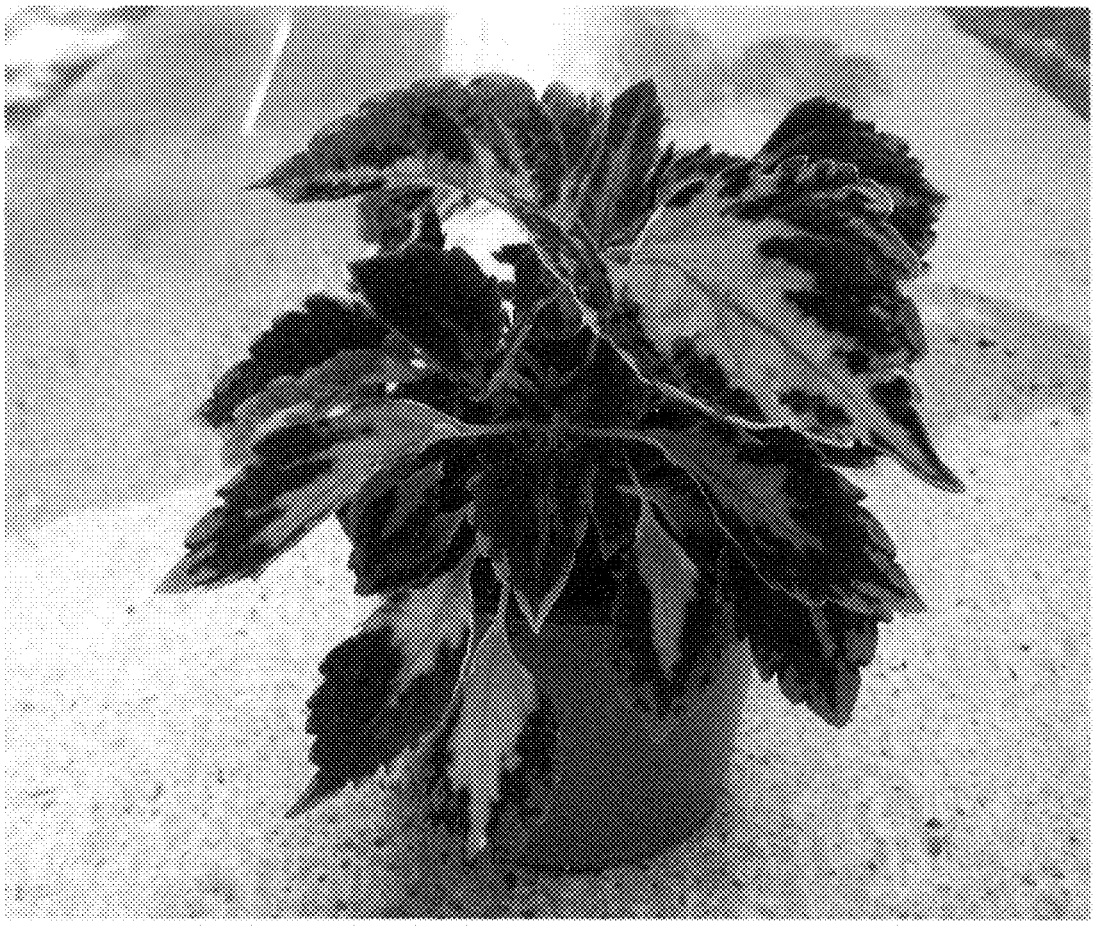

* * * * *